(12) United States Patent
Robinson

(10) Patent No.: US 9,585,766 B2
(45) Date of Patent: Mar. 7, 2017

(54) EXPANDABLE INTERVERTEBRAL CAGE ASSEMBLIES AND METHODS

(71) Applicant: Spectrum Spine IP Holdings, LLC, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 176 days.

(21) Appl. No.: 13/962,879

(22) Filed: Aug. 8, 2013

(65) Prior Publication Data

US 2014/0148904 A1     May 29, 2014

Related U.S. Application Data

(60) Provisional application No. 61/680,729, filed on Aug. 8, 2012, provisional application No. 61/787,744, filed on Mar. 15, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30382* (2013.01); *A61F 2002/30448* (2013.01); *A61F 2002/30451* (2013.01); *A61F 2002/30457* (2013.01); *A61F 2002/30471* (2013.01); *A61F 2002/30492* (2013.01); *A61F 2002/30515* (2013.01); *A61F 2002/30579* (2013.01); *A61F 2002/30594* (2013.01); *A61F 2002/30598* (2013.01); *A61F 2002/30629* (2013.01); *A61F 2002/30736* (2013.01); *A61F 2002/30827* (2013.01)

(58) Field of Classification Search
CPC .... A61F 2/44; A61F 2/4425; A61F 2002/443; A61F 2/4455; A61F 2/447; A61F 2002/4475; A61F 2/442
See application file for complete search history.

(56) References Cited

U.S. PATENT DOCUMENTS

| | | | |
|---|---|---|---|
| 4,545,374 A | 10/1985 | Jacobson | |
| 5,653,763 A | 8/1997 | Errico et al. | |
| 6,102,950 A | 8/2000 | Vaccaro | |
| 6,176,882 B1 * | 1/2001 | Biedermann et al. | 623/17.15 |

(Continued)

FOREIGN PATENT DOCUMENTS

| | | | |
|---|---|---|---|
| EP | 1504735 | 1/2008 | |
| FR | 2771282 A1 * | 5/1999 | ............ A61F 2/44 |
| WO | 2011124787 | 10/2011 | |

*Primary Examiner* — Eduardo C Robert
*Assistant Examiner* — Julianna N Harvey
(74) *Attorney, Agent, or Firm* — FisherBroyles, LLP; Anthony J. DoVale

(57) ABSTRACT

An expandable assembly for insertion into an intervertebral space is presented. The assembly, in particular aspects, includes an elongate body comprising an upper portion and a lower portion, wherein the elongate body defines an internal longitudinal channel extending from a proximal opening to a distal cavity. The assembly may include an expander that is sized and shaped for insertion into the distal cavity, thereby selectively expanding the upper portion away from the lower portion. The elongate body may also include one or more bone graft windows a cap that is sized and shaped for insertion into the proximal opening.

28 Claims, 10 Drawing Sheets

(56) References Cited

U.S. PATENT DOCUMENTS

| | | |
|---|---|---|
| 6,436,140 B1* | 8/2002 | Liu ..................... A61F 2/446 623/17.11 |
| 6,454,807 B1* | 9/2002 | Jackson ................. 623/17.15 |
| 6,582,431 B1 | 6/2003 | Ray |
| 6,641,614 B1* | 11/2003 | Wagner et al. ............ 623/17.15 |
| 6,849,093 B2* | 2/2005 | Michelson ................ 623/17.15 |
| 6,893,464 B2 | 5/2005 | Kiester |
| 6,902,547 B2 | 6/2005 | Aves |
| 7,128,760 B2* | 10/2006 | Michelson .............. A61F 2/446 606/247 |
| 7,431,735 B2 | 10/2008 | Liu et al. |
| 7,674,297 B2 | 3/2010 | Falahee |
| 8,007,537 B2 | 8/2011 | Zucherman et al. |
| 8,105,382 B2 | 1/2012 | Olmos et al. |
| 2002/0068977 A1* | 6/2002 | Jackson ................. 623/17.15 |
| 2002/0128713 A1 | 9/2002 | Ferree |
| 2005/0015149 A1 | 1/2005 | Michelson |
| 2006/0129244 A1 | 6/2006 | Ensign |
| 2006/0206207 A1* | 9/2006 | Dryer et al. .............. 623/17.11 |
| 2007/0270968 A1 | 11/2007 | Baynham |
| 2008/0161919 A1 | 7/2008 | Melkent |
| 2010/0222816 A1 | 9/2010 | Gabelberger |
| 2011/0093074 A1* | 4/2011 | Glerum et al. ............ 623/17.16 |
| 2011/0319997 A1* | 12/2011 | Glerum et al. ............ 623/17.15 |
| 2012/0059473 A1* | 3/2012 | Weiman ................... A61F 2/44 623/17.16 |
| 2012/0143341 A1 | 6/2012 | Zipnick |

* cited by examiner

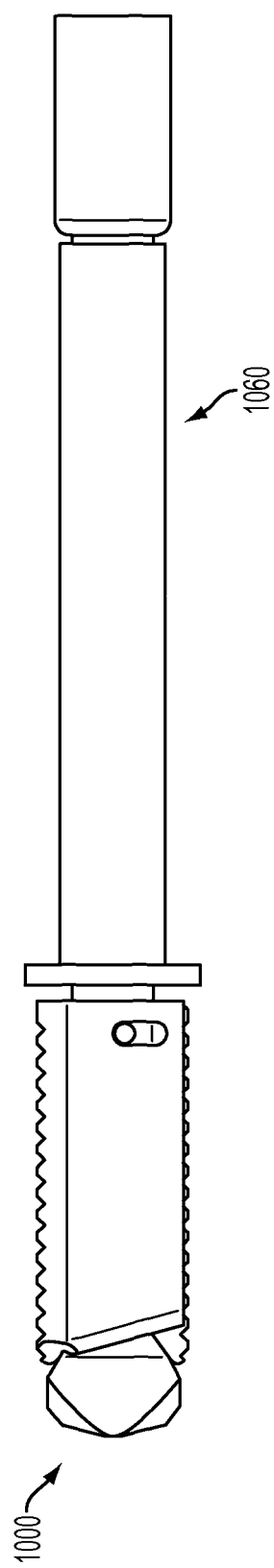
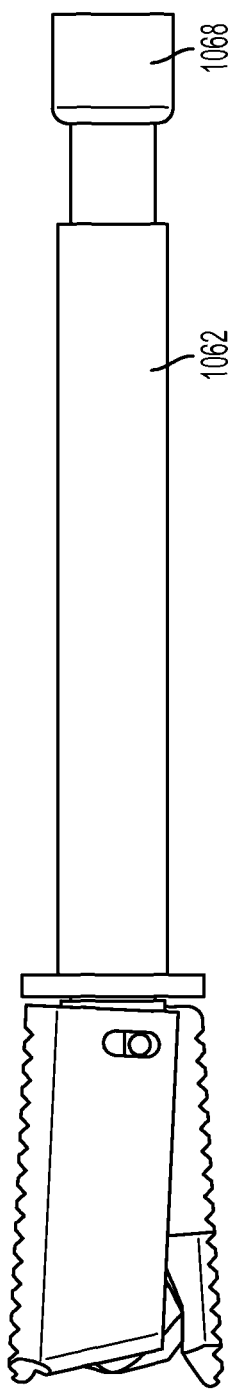
FIG. 6A
FIG. 6B

EXPANDABLE INTERVERTEBRAL CAGE ASSEMBLIES AND METHODS

CONTINUITY

This application claims the benefit of and priority to U.S. Application No. 61/680,729, titled EXPANDABLE INTERVERTEBRAL CAGE ASSEMBLIES AND METHODS, filed on Aug. 8, 2012 and U.S. Application No. 61/787,744, titled EXPANDABLE INTERVERTEBRAL CAGE ASSEMBLIES AND METHODS, filed on Mar. 15, 2013, both of which are incorporated herein in their entirety.

BACKGROUND

The following disclosure relates generally to medical devices, systems and methods, including, for example, systems and methods for lumbar interbody fusion.

Surgical implantation of disc replacement material is typically used to provide support along the spinal column in cases where a portion of the patient's intervertebral anatomy has become weakened, diseased, or destroyed. Such support systems are also commonly used following a discectomy, where an intervertebral disc is surgically removed.

Most commonly, existing support systems typically operate by inhibiting normal movement between the adjacent vertebrae, thereby holding these vertebrae at fixed positions relative to one another, with the mechanical body of the supporting structure providing the needed support along the patient's spinal column. Such supporting systems are typically made of stainless steel, titanium, polymer (e.g., an organic polymer thermoplastic such as polyether ether ketone (PEEK)), carbon fiber, or ceramic and they are designed to permanently remain within the patient's body.

It is beneficial, in addition to fixation, to try to stimulate bone growth between the adjacent vertebrae. To do so, spine surgeons use bone graft material in addition to fixation devices. Bone graft doesn't heal or fuse the spine immediately; instead, bone graft provides a foundation or scaffold for the patient's body to grow new bone. Bone graft can stimulate new bone production. When new bone grows and solidifies, fusion occurs. Although instrumentation (e.g., screws, rods) is often used for initial stabilization (post-operative), it is the healing of bone that welds vertebrae together to create long-term stability. There are two general types of bone grafts: real bone and bone graft substitutes. Real bone can come from the patient (autograft) or from a donor bone (allograft). Also used in these types of surgery are bone substitute, osteoinductive agent, and bone cement.

There is a need for improved systems and methods for lumbar interbody fusion.

SUMMARY

An expandable assembly for insertion into an intervertebral space is disclosed. The assembly, in particular aspects, includes an elongate body comprising an upper portion and a lower portion, wherein the elongate body defines an internal longitudinal channel extending from a proximal opening to a distal cavity. The assembly may include an expander that is sized and shaped for insertion into the distal cavity, thereby selectively expanding the upper portion away from the lower portion. The elongate body may also include one or more bone graft windows a cap that is sized and shaped for insertion into the proximal opening.

BRIEF DESCRIPTION OF THE DRAWINGS

These and other features of the preferred embodiments of the present invention will become more apparent in the detailed description in which reference is made to the appended drawings wherein:

FIG. 6A is a side elevational view of an expandable cage in an unexpanded position associated with an insertion tool;

FIG. 6B is a side elevational view of an expandable cage in an expanded position associated with an insertion tool;

DETAILED DESCRIPTION

Figure 1A:
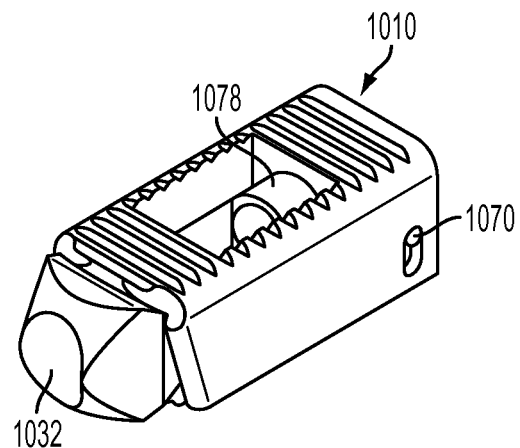
FIG. 1A is a perspective view of one aspect of an expandable cage for insertion into an intervertebral space in an unexpanded position.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein are systems, tools, and methods for supporting adjacent vertebrae of the spine, for example, as part of interbody spinal fusion surgery. Although the systems, tools, and methods are presented herein in the context of posterior lumbar interbody fusion (PLIF), direct lateral interbody fusion (DLIF), and transforaminal lumbar interbody fusion (TLIF), the assemblies and techniques may be useful in a variety of therapeutic contexts.

In one aspect, a cage assembly for the stabilization of an intervertebral space during a spinal fusion procedure is presented. As described herein, the cage assembly may comprise an expander such as an expansion screw or a shim which, when inserted, selectively expands the body of the cage assembly to a desired size. The cage assembly may include one or more openings or windows for receiving bone fusion material. The bone fusion material may comprise, for example and without limitation, autologous bone, allograft bone, bone substitute, osteoinductive agent, and/or bone cement. The cage assembly may also include a plug or cap to contain the bone fusion material and to add strength to the trailing side of the cage in weight bearing.

In one aspect, a cage assembly 1000 may include a generally elongate cage body 1010, an expander 1032, and an insertion tool 1060, as shown in FIG. 1A.

The cage body 1010 may be generally rectangular in cross-section. The body 1010 may include an upper portion 1012 and a lower portion 1018. The outer surfaces of the two portions 1012, 1018 may be ridged or grooved, laterally, as shown. The two portions 1012, 1018 may be joined together by a pin-in-slot joint or another type of hinge 1070 near the proximal end. The space between the two portions 1012, 1018 may form an internal passage or channel 1020 that extends lengthwise through the cage body 1010. The cage body 1010 may also include one or more openings or windows 1050 for receiving bone fusion material.

Figure 1B:
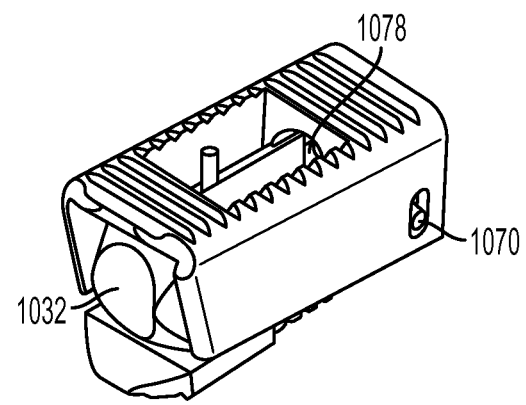
FIG. 1B is a perspective view of the expandable cage of FIG. 1A in an expanded position.

As illustrated in FIG. 1A and FIG. 1B, the expander 1032 may be a keyed shim. Referring to the perspective view in FIG. 1A, the shim has "key" on its distal portion. In this particular aspect, the key is generally conical in cross-section with a rectangular or square end, like the head of a bolt, and tapered on both sides. The key shape on the distal portion may be sized and shaped to fit within a distal cavity 1030, as shown in Section A-A. In one aspect, the expander 1032 may include a set of keyed shims, each key having a discrete size and shape. The cage body 1010 may also include a number of cage bodies, each with a distal cavity 1030 having a different size and shape. The size and shape of the key, together with its matching distal cavity 1030, may be used to create a cage body 1010 that opens to a desired height and angular orientation.

Figure 2A:
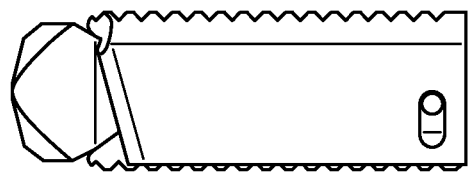
FIG. 2A is a side elevational view of the expandable cage of FIG. 1A in the unexpanded position.

Referring again to the perspective view in FIG. 1A, the proximal end of the keyed shim may include a proximal portion 1078, which can be seen through the window 1050 in the upper portion 1012. The proximal portion 1078 of the shim may include a socket or other feature for receiving the distal end of an insertion tool 1060. The tool may be used to pull the keyed shim 1032 proximally until the key slides into the distal cavity. One aspect of a keyed shim 1032 is also illustrated in FIG. 2. As shown, the proximal portion 1078 may be generally cylindrical in shape and may be suitable for grasping by the distal end of an insertion tool. The keyed shim 1032, as shown, may also include side rails that are sized and shaped to engage with interior portions of the cage body 1010.

The insertion tool 1060, as shown in FIG. 1B, may include a cannula 1062 and a drive rod 1068. The distal end of the drive rod 1068 may include a specialized head or other tool for grasping or otherwise engaging the proximal portion 1078 of the keyed shim; e.g., a threaded portion. Once engaged, the drive rod 1068 may be used to pull the keyed shim proximally, or push it distally, into a desired position. Alternatively, the threaded rod may be rotated in order to actuate a change in the position of the expander 1032 to the desired position.

As shown in FIG. 1B, the expander 1032 or keyed shim, when pulled proximally and into the distal cavity 1030, will cause the two portions 1012, 1018 of the cage body 1010 to expand or spread open. The pin-in-slot joint or hinge 1070 may allow the two portions 1012, 1018 to expand or move vertically relative to one another, while also allowing the two portions 1012, 1018 to rotate about the hinge 1070 thereby changing the angle of the upper portion 1012 and the bottom portion 1018 of the body. In this aspect, the keyed shim 1032 may induce an angular relationship in which the distal end of the cage body 1010 becomes more open than the proximal end. The cage body 1010, as shown, may also include a set screw 1042 for insertion into the proximal portion 1078 of the keyed shim. The drive rod 1068 or another tool inserted through the cannula 1062 may be used to rotate or otherwise drive the set screw 1042 into position. The set screw 1042, in one aspect, may be sized and shaped to retain the expander 1032 firmly within its final position, such that the expander 1032 will not retreat or otherwise "back out" unless purposely driven by a tool, also aiding in containment of the fusion material within the cage assembly and strengthening the proximal wall of the construct.

In use, the cage assembly 1000 may be inserted using an insertion tool 1060 into an intervertebral space; for example, in the lumbar region of the spine. A drive rod 1068 or other tool may be used to grasp or otherwise engage with a proximal portion 1078 of the expander 1032, and pull the expander 1032 proximally until its distal "key" is seated within a distal cavity 1030. Section B-B of FIG. 1B shows the key of the expander 1042 seated within the distal cavity 1030.

Figure 5A:
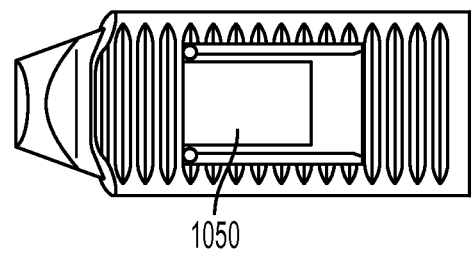
FIG. 5A is a top plan view of the expandable cage of FIG. 1A in the unexpanded position.
Figure 5B:
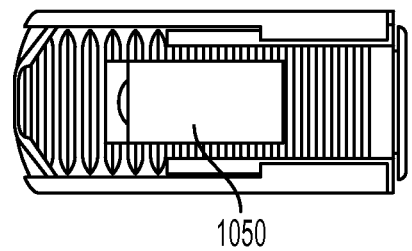
FIG. 5B is a top plan view of the expandable cage of FIG. 1A in the expanded position.
Figure 7:
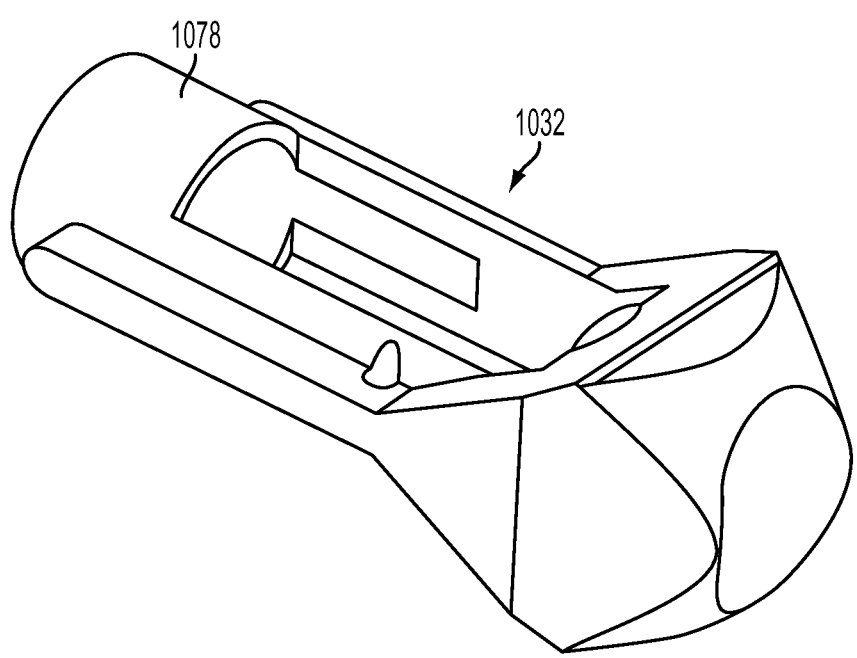
FIG. 7 is a perspective view of an expander for use in an expandable cage.
Figure 8A:
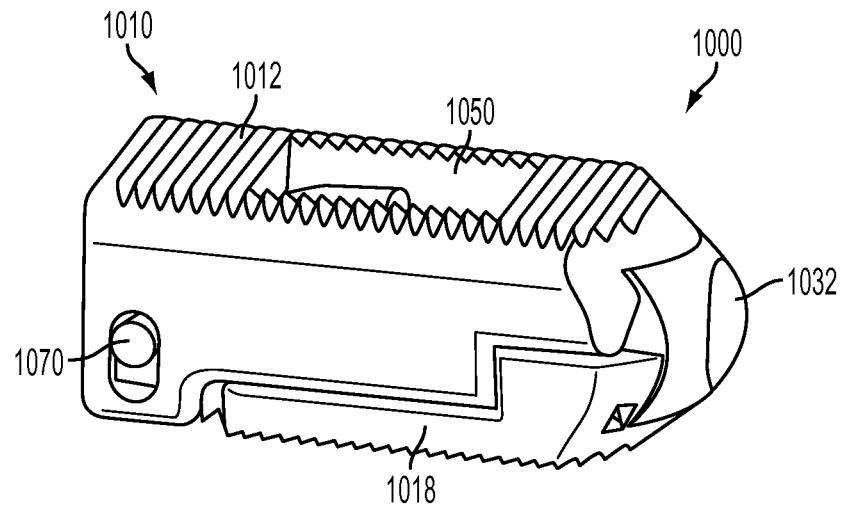
FIG. 8A is a perspective view of one aspect of an expandable cage in the unexpanded position.
Figure 8B:
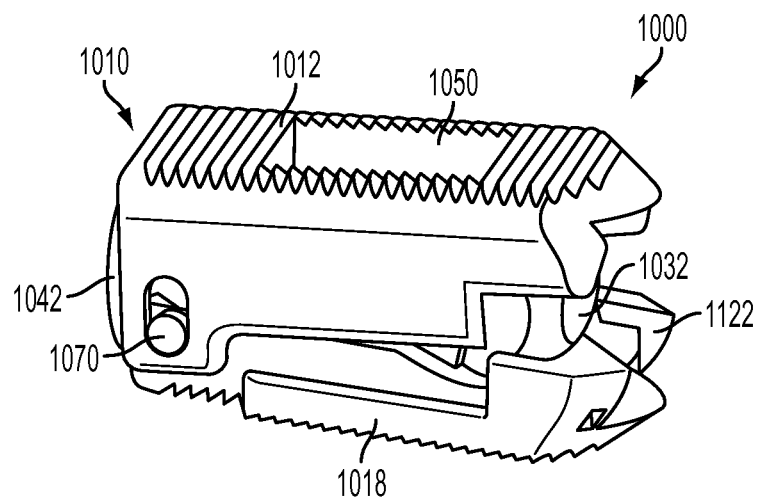
FIG. 8B is a perspective view of the expandable cage of FIG. 8A in the expanded position, showing at least one tongue in the distal end of the upper and lower portions for complimentary fit into a recess defined therein the expander.
Figure 9A:
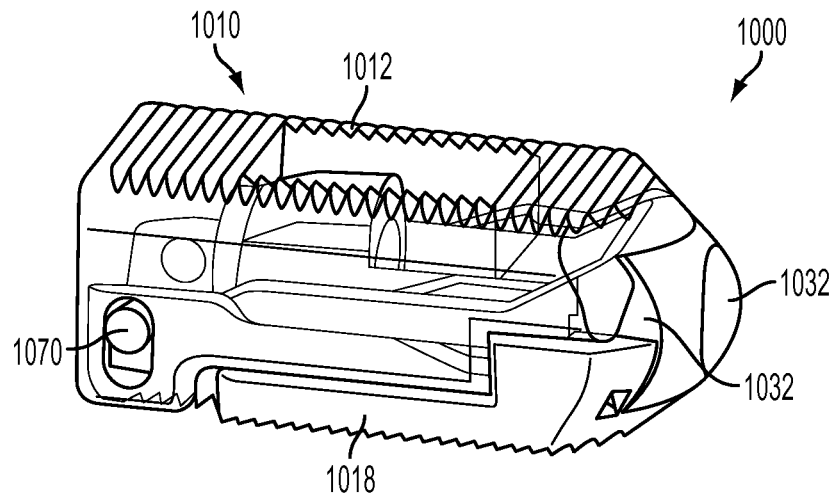
FIG. 9A is a partially transparent perspective view of FIG. 8A.
Figure 9B:
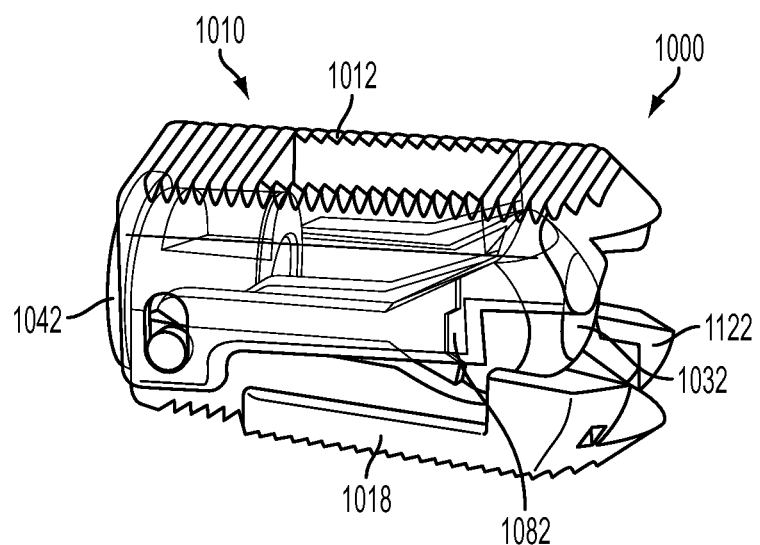
FIG. 9B is a partially transparent perspective view of FIG. 8B.

In certain exemplified aspects, the cage assembly 1000 comprises means to prevent the separation of the upper portion 1012 and the lower portion 1018 prior to expansion. In one aspect, the distal portion 1080 of the shim 1032 defines at least one substantially longitudinal slot, groove, or recess 1082. As shown in the figures, the distal portion of the shim can define a slot, groove, or recess on either side surface 1084. In this aspect, the distal end 1113 of the upper portion 1012 and the distal end 1119 of the lower portion 1018 each comprise a tongue 1120, 1122 sized such that both tongues can slide into and be retained within one of the recesses 1082 defined in the distal portion of the shim. The upper and lower portion can also have bilateral tongues, as shown in the figures. Referring to FIGS. 5 and 6, in the unexpanded position, the tongues from both the upper and lower portion are retained within the recess(es) by portions of the shim. This permits insertion of the cage without the potential of the premature separation of the upper and lower portions. As the shim is moved proximately, the recess is moved proximately, while the tongues remain unmoved, essentially disengaging the tongues and recesses. Once the shim is moved sufficiently, the tongues disengage from the recess, enabling the upper and lower portions to expand as designed.

Figure 10:
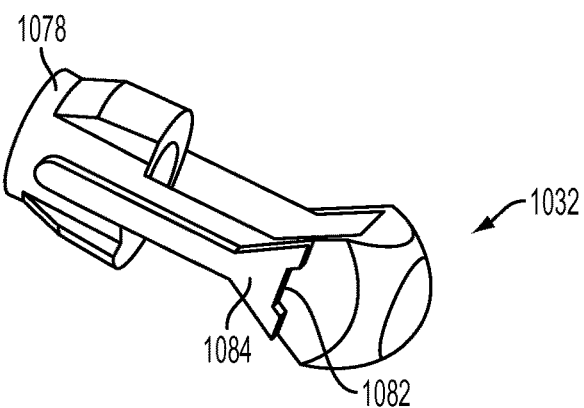
FIG. 10 is a perspective view of the expander of FIGS. 8A and 8B.
Figure 11:
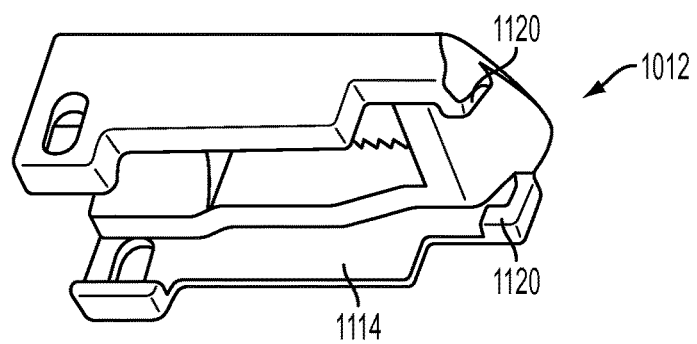
FIG. 11 is a perspective view of the upper portion of FIGS. 8A and 8B.
Figure 12:
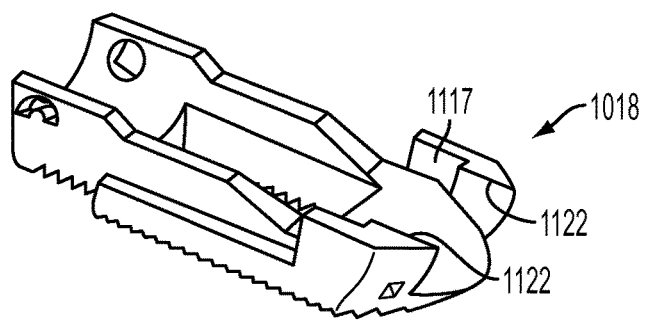
FIG. 12 is a perspective view of the lower portion of FIGS. 8A and 8B.
Figure 13A:
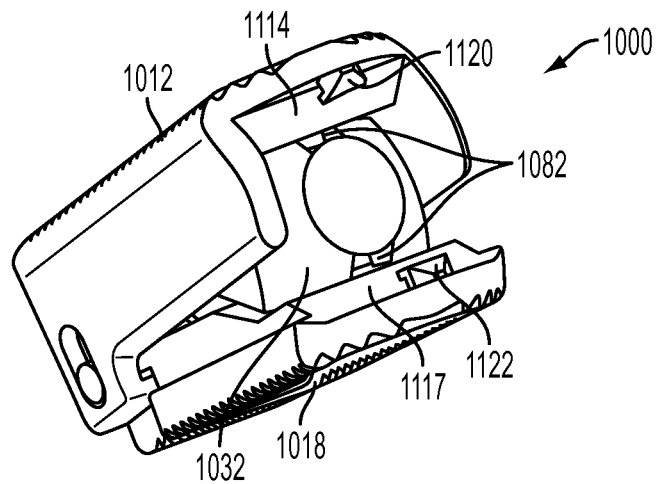
FIG. 13a is a perspective view of one aspect of an expandable cage in the expandable position, showing at least one hook positioned on the inner surface of the upper and lower portions configured for complimentary receipt into a recess defined in the distal portion of the expander.
Figure 13B:
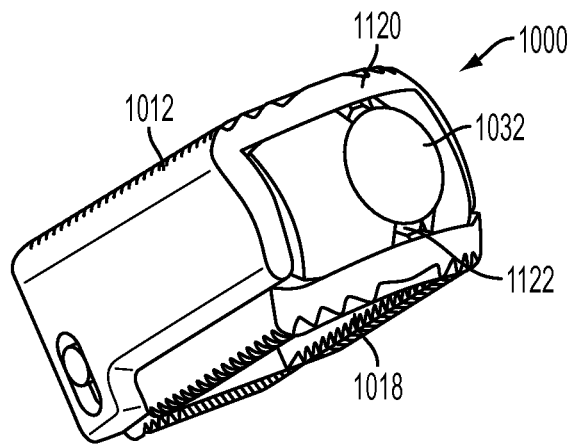
FIG. 13b is a perspective view of the expandable cage of FIG. 13a in the unexpanded position.

In another exemplified aspect, as illustrated in FIGS. 10 and 11, the upper and lower portions can comprise a tongue, pin, or hook 1120, 1122 positioned on each of their inner surfaces 1114, 1117. In this aspect, the distal portion of the shim defines a recess, slot, or hollow corresponding to each tongue, pin or hook such that, when the cage is in the unexpanded position, the hooks of the upper and lower portions are retained within the slots in the distal portion of the shim. As the shim is moved proximately, the slots are also moved proximately, while the hooks remain unmoved, essentially disengaging the hooks and slots and permitting expansion of the upper and lower portions.

In still another aspect, the upper and lower portions may be bonded together in a temporary fashion so they do not splay during insertion. For instance, a portion of the lower portion may be ultrasonically welded, glued, or otherwise bonded to a portion of the upper portion. Then, after insertion, the bond can be broken during and by the expansion of the of the upper and lower portions. It is also contemplated that the bond can be between the upper and/or lower portion and the insert.

Bone fusion material may be inserted into the one or more windows 1050 into the cage body 1010 as well as through the aperture in the proximal end of the expander 1078, and thereby into the proximity of the surrounding bony structures, in order to promote fusion and to further secure the cage assembly 1000 in place.

Either before or after placement of the bone fusion material, a cap or set screw 1042 may be inserted (using a drive rod 1068 or another tool inserted through the cannula 1062) into the proximal portion 1078 of the shim. The set screw 1042 helps contain the bone fusion material and also strengthens the proximal end wall of the cage body 1010.

Also presented herein is a method for inserting and expanding a cage assembly within an intervertebral space in the spine.

In use, the cage assembly 1000 may be inserted into an intervertebral space; for example, in the lumbar region of the spine. An expander 1032 may be inserted through the proximal opening in the body 1010. The expander 1032 may be driven by a tool so that it drives apart the two portions 1012, 1018 of the body 1010. In one aspect, the body 1010 is selectively expandable because the expander 1032 may be inserted and/or counter-inserted until the body 1010 achieves the size and shape desired by the surgeon.

Bone fusion material may be inserted into the one or more windows 1050 into the body 1010, and thereby into the proximity of the surrounding bony structures, in order to further secure the cage assembly 1000 in place.

Figure 2B:
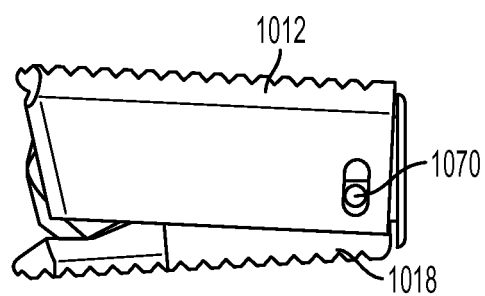
FIG. 2B is a side elevational view of the expandable cage of FIG. 1A in the expanded position.
Figure 3A:
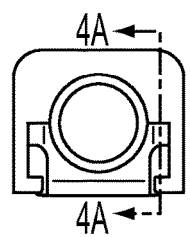
FIG. 3A is a proximal end elevational view of the expandable cage of FIG. 1A in the unexpanded position.
Figure 3B:
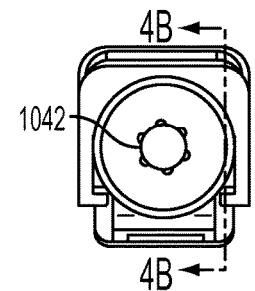
FIG. 3B is a proximal end elevational view of the expandable cage of FIG. 1A in the expanded position.
Figure 4A:
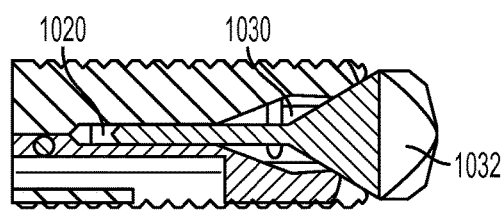
FIG. 4A is a side elevational cut away view of the expandable cage of FIG. 1A in the unexpanded position, cut along line 4A-4A in FIG. 3A.
Figure 4B:
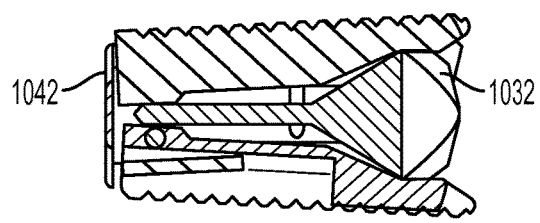
FIG. 4B is a side elevational cut away view of the expandable cage of FIG. 1A in the expanded position, cut along line 4B-4B in FIG. 3B.

A cap 1042 such as the cap screw shown in FIG. 2B may be inserted into the proximal end of the body 1010. The cap 1042 helps contain the bone fusion material and also strengthens the proximal end wall of the cage body 1010.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed herein above, and that many modifications and other aspects are intended to be included within the scope of the appended claims. Moreover, although specific terms are employed herein, as well as in the claims which follow, they are used only in a generic and descriptive sense, and not for the purposes of limiting the described invention, nor the claims which follow.

I claim:

1. An expandable cage system for inserting an expandable cage into an intervertebral space comprising:
a cage body having an upper portion and a lower portion, the upper portion comprising a substantially planar upper portion outer surface and an upper portion inner surface and the lower portion comprising a substantially planar lower portion outer surface and a lower portion inner surface, wherein the upper portion and the lower portion define an internal passage therebetween; and
a monolithic elongate expander at least partially positioned therebetween the upper portion and the lower portion and in the internal passage, wherein the expander is configured to move proximally relative to the upper and lower portions from a first position to a second position, the expander comprising a distal nose portion to facilitate insertion into the intervertebral space, wherein in the first position, the expandable cage is unexpanded and the distal nose portion extends at least partially distally past a distal portion of the cage body, and wherein in the second position, the expandable cage is expanded, increasing the space between the upper portion outer surface and the lower portion outer surface, wherein the upper portion and lower portion are hingedly connected to one another at a hinge point to permit vertical movement of the upper portion relative to the lower portion at the hinge point while also permitting the upper portion and the lower portion to rotate about the hinge point, thereby changing the angle of the upper portion relative to the lower portion; and an insertion tool configured to engage a proximal end of the expandable cage, insert it into a desired position in the intervertebral space, and move the expander from the first position to the second position.

2. The system of claim 1, wherein the insertion tool moves the expander from the first position to the second position by pulling the expander proximally.

3. The system of claim 1, wherein the upper portion has an upper portion inner surface and the lower portion has a lower portion inner surface, and wherein portions of the distal portion of the expander are complimentarily shaped with at least one of the upper portion inner surface and the lower portion inner surface, whereby pulling the expander proximally cams the distal portion of the expander against the at least one of the upper portion inner surface and the lower portion inner surface to expand the cage body.

4. The system of claim 1, further comprising a means to retain the cage body in the unexpanded position and resist expansion during insertion of the expandable cage into the intervertebral space.

5. The system of claim 1, wherein the proximal portion of the cage body defines an aperture in communication with the internal passage.

6. The system of claim 5, further comprising a set screw sized and shaped to complimentarily fit within the aperture and retain the expander in the second position.

7. The system of claim 1, wherein a portion of the distal portion of the expander comprises a first side surface and a second side surface, wherein one of the side surfaces defines at least one substantially longitudinal slot.

8. The system of claim 7, wherein the distal end of the upper portion and the distal end of the lower portion each comprise a tongue sized for a complimentary fit within the at least one substantially longitudinal slot when the cage body is in the unexpanded position, and wherein moving the expander into the second position moves the tongue out of engagement with the substantially longitudinal slot.

9. The system of claim 8, wherein the upper and lower portions comprise bilateral tongues.

10. The system of claim 1, wherein the distal end of the upper and lower portions each comprise a hook positioned thereon the respective inner surface.

11. The system of claim 10, wherein the distal portion of the expander defines recesses for complimentary receipt of the respective hooks when the cage body is in the unexpanded position, and wherein moving the expander into the second position moves the hooks out of engagement with the recesses.

12. The system of claim 1, wherein a portion of the distal end of the upper portion and a portion of the distal end of the lower portion are bonded together when the cage body is in the unexpanded position, and wherein moving the expander into the second position breaks the bond, allowing the cage body to move into the expanded position.

13. The system of claim 1, wherein the cage body defines one or more windows in communication with the internal passage.

14. The system of claim 1, wherein the distal nose portion is integral with the elongate expander.

15. An expandable cage for insertion into an intervertebral space comprising:

a cage body having an upper portion and a lower portion, the upper portion comprising a substantially planar upper portion outer surface and an upper portion inner surface and the lower portion comprising a substantially planar lower portion outer surface and a lower portion inner surface, wherein the upper portion and lower portion are hingedly connected to one another at a hinge point to permit vertical movement of the upper portion relative to the lower portion at the hinge point while also permitting the upper portion and the lower portion to rotate about the hinge point, thereby changing the angle of the upper portion relative to the lower portion, and wherein the upper portion and the lower portion define an internal passage therebetween; and a monolithic elongate expander at least partially positioned therebetween the upper portion and the lower portion and in the internal passage, wherein the expander is configured to move proximally relative to the upper and lower portions from a first position to a second position, the expander comprising a distal nose portion to facilitate insertion into the intervertebral space, wherein in the first position, the expandable cage is unexpanded and the distal nose portion extends at least partially distally past a distal portion of the cage body, and wherein in the second position, the expandable cage is expanded, increasing the space between the upper portion outer surface and the lower portion outer surface.

16. The expandable cage of claim 15, wherein the distal nose portion is integral with the elongate expander.

17. The expandable cage of claim 15, wherein the expander moves from the first position to the second position by pulling the expander proximally.

18. The expandable cage of claim 15, wherein the upper portion has an upper portion inner surface and the lower portion has a lower portion inner surface, and wherein portions of the distal portion of the expander are complimentarily shaped with at least one of the upper portion inner surface and the lower portion inner surface, whereby pulling the expander proximally cams the distal portion of the expander against the at least one of the upper portion inner surface and the lower portion inner surface to expand the cage body.

19. The expandable cage of claim 15, further comprising a means to retain the cage body in the unexpanded position and resist expansion during insertion of the expandable cage into the intervertebral space.

20. The expandable cage of claim 15, wherein the proximal portion of the cage body defines an aperture in communication with the internal passage.

21. The expandable cage of claim 20, further comprising a set screw sized and shaped to complimentarily fit within the aperture and retain the expander in the second position.

22. The expandable cage of claim 15, wherein a portion of the distal portion of the expander comprises a first side surface and a second side surface, wherein one of the side surfaces defines at least one substantially longitudinal slot.

23. The expandable cage of claim 22, wherein the distal end of the upper portion and the distal end of the lower portion each comprise a tongue sized for a complimentary fit within the at least one substantially longitudinal slot when the cage body is in the unexpanded position, and wherein moving the expander into the second position moves the tongue out of engagement with the substantially longitudinal slot.

24. The expandable cage of claim 23, wherein the upper and lower portions comprise bilateral tongues.

25. The expandable cage of claim 15, wherein the distal end of the upper and lower portions each comprise a hook positioned thereon the respective inner surface.

26. The expandable cage of claim 25, wherein the distal portion of the expander defines recesses for complimentary receipt of the respective hooks when the cage body is in the unexpanded position, and wherein moving the expander into the second position moves the hooks out of engagement with the recesses.

27. The expandable cage of claim 15, wherein a portion of the distal end of the upper portion and a portion of the distal end of the lower portion are bonded together when the cage body is in the unexpanded position, and wherein moving the expander into the second position breaks the bond, allowing the cage body to move into the expanded position.

28. The expandable cage of claim 15, wherein the cage body defines one or more windows in communication with the internal passage.

\* \* \* \* \*